(12) United States Patent
Gamboa Burgos

(10) Patent No.: US 11,628,089 B2
(45) Date of Patent: Apr. 18, 2023

(54) APPLICATOR FOR OPHTHALMIC SOLUTIONS IN SINGLE-DOSE CONTAINERS AND A KIT CONTAINING SAME

(71) Applicant: Alejandro Gamboa Burgos, Lima (DE)

(72) Inventor: Alejandro Gamboa Burgos, Lima (DE)

( * ) Notice: Subject to any disclaimer, the term of this patent is extended or adjusted under 35 U.S.C. 154(b) by 0 days.

(21) Appl. No.: 17/284,941

(22) PCT Filed: Oct. 15, 2018

(86) PCT No.: PCT/PE2018/000022
§ 371 (c)(1),
(2) Date: Apr. 13, 2021

(87) PCT Pub. No.: WO2020/080962
PCT Pub. Date: Apr. 23, 2020

(65) Prior Publication Data
US 2021/0378863 A1    Dec. 9, 2021

(51) Int. Cl.
*A61F 9/00*    (2006.01)
*C08K 3/015*   (2018.01)
*C08K 3/08*    (2006.01)

(52) U.S. Cl.
CPC ............ *A61F 9/0026* (2013.01); *C08K 3/015* (2018.01); *C08K 2003/0806* (2013.01)

(58) Field of Classification Search
CPC ............ A61F 9/0026; A61F 2009/0052; A61F 9/0008; B65D 1/08; B65D 1/32; B65D 47/18; B65D 47/20
USPC .................................................. 222/421, 420
See application file for complete search history.

(56) References Cited

U.S. PATENT DOCUMENTS

| | | | |
|---|---|---|---|
| 4,685,906 A * | 8/1987 | Murphy ................ | A61F 9/0026 604/300 |
| 4,960,407 A | 10/1990 | Cope | |
| 5,499,751 A * | 3/1996 | Meyer ................... | A61F 9/0008 222/189 |
| 9,078,806 B2 * | 7/2015 | Berner ...................... | A61J 1/10 |
| 2005/0101921 A1 | 5/2005 | Sherman | |
| 2008/0208148 A1 | 8/2008 | Soon et al. | |
| 2008/0283530 A1* | 11/2008 | Lee ....................... | A61F 9/0008 220/315 |

(Continued)

FOREIGN PATENT DOCUMENTS

WO    2004043315 A1    5/2004

*Primary Examiner* — Erich G Herbermann
*Assistant Examiner* — Seth Han
(74) *Attorney, Agent, or Firm* — Pearson IP; Loren Donald Pearson

(57) ABSTRACT

An applicator for ophthalmic solutions in single-dose containers includes a structure, an oval rim, a container attachment portion, a hollow and flat support base, and additional features. The structure with open spaces is for inserting, removing, and pressing the single-dose container and allowing the label and the contents of the container to be viewed. The oval rim has a concave upper lip and a concave lower lip to facilitate the positioning of the applicator at an angle between 30 and 60° with respect to a horizontal plane. The features of the applicator enable the device to be used easily, ergonomically, comfortably, and ensure a safe use of the single-dose container in applications after the first use.

11 Claims, 9 Drawing Sheets

(56) References Cited

U.S. PATENT DOCUMENTS

2010/0286634 A1* 11/2010 Marx .................. A61F 9/0026
604/302

* cited by examiner

APPLICATOR FOR OPHTHALMIC SOLUTIONS IN SINGLE-DOSE CONTAINERS AND A KIT CONTAINING SAME

FIELD OF THE INVENTION

The present invention falls within the technical field of ophthalmic product dispensers. Specifically, an applicator for ophthalmic solutions in single-dose containers or disposable bottles with a flat handle portion is disclosed.

BACKGROUND OF THE INVENTION

The prior art documents found closest to the present invention are cited below.

This prior art includes patent document US20050101921A1, published on 12 May 2005, titled "Dropper positioning device", which relates to a device that assists in positioning eye drops from a bottle, preferably single-dose containers. This invention comprises an eye guide which is preferably oval in shape, a substantially rigid extension portion attached to the eye guide, and a bottle attachment portion attached to a second end of the extension portion, said bottle attachment portion further comprising a base portion attached to the rigid extension portion, said base portion including a slot which is sized to receive a single-use disposable bottle with a flat handle portion which has a pair of compression tabs located on opposite sides of the slot. In a preferred embodiment, said invention comprises a positioning indicator for proper positioning of a disposable bottle having a flat handle portion.

Another prior art document is US20080208148A1, published on 25 May 2005, titled "Ophthalmic Device", which discloses an ophthalmic device for assisting in the accurate dispensing of an ophthalmic substance into an eye, said device comprising an elastic oval rim having an open end and an opening at the opposite end. The periphery of the open end is adapted to receive and secure the nozzle associated with an eye drop dispenser. The opening may take the form of an asterisk so that an eye drop container can be fitted and secured in it. FIG. 2 of said document shows that, from a front view, the oval rim has lips that are concave with respect to the structure, to ergonomically adjust to the eye.

Another prior art document is U.S. Pat. No. 4,960,407A, published on 26 May 1989, titled "Disposable eye drop dispenser instrument for post-surgical and general use", which comprises a generally oval or periorbital ring contoured to fit within the orbital or periorbital area of a patient's body and at least one post extending from the oval ring generally perpendicular to a plane of the oval ring, the post being attached to the neck and shoulder region of the bottle. In a preferred embodiment at least one post extends to the rear of the container where a cradle base will be located.

The prior art also includes document WO2004043315A, published on 27 May 2004, titled "A device and method for facilitating the application of liquid material to the eye", which relates to a device for facilitating the application of liquid material to the eye, which has an outlet opening configured so as to substantially prevent adherence of liquid drops to same. The device has a support means which can be abutted against an eyelid and which can be used to evert the eyelid. When a liquid dispenser is placed on the support, eye drops or other liquid for application to an eye can be applied to the eye in an optimal position from an outlet opening of the liquid dispenser, to allow easy one-handed application.

This invention also relates to a liquid dispenser having an integral support for abutting against and everting an eyelid. In a preferred embodiment, the support material may be of a substantially elastic material.

However, not a single ophthalmic substance applicator device in single-dose containers has been found in the prior art which integrates a set of advantageous technical features, with extremely useful benefits for the user, such as allowing to be positioned on the eye at an angle of 30° to 60° with respect to a horizontal plane facilitating the application of the ophthalmic solution, allowing to hold the single-dose container in a vertical position with the mouth of the container upwards when not in use, with a structure allowing to keep the container isolated from any physical contact with flat external surfaces, with open spaces in the structure for inserting, removing and pressing the container directly with the fingers, and to substantially view the contents and the label of the container, making it possible to use the single-dose container in applications after the first use, among other advantages considered important in the proposed invention.

SUMMARY OF THE INVENTION

The present invention relates to a device for applying ophthalmic solutions, specifically eye drops in single-dose containers, comprising:
a fixed structure (1) with one or more walls (2) covering the length, width and height of a single-dose container, wherein the one or more walls (2) leave at least one open space (2A) for inserting, removing, pressing the container and allowing the label and the contents of the container to be viewed;
a flat hollow support base (3) attached to or forming part of one end of the one or more walls of the solid structure, where the flat part of the support base allows the single-dose container to be held upright with the mouth of the container facing upwards when not in use, and the hollow part of the support base allows a finger to be inserted to remove the single-dose container;
an oval rim (4) located at the other end of the one or more walls (2) of the solid structure, the oval rim having an upper lip (5) and a lower lip (6), which are concave at an offset to facilitate positioning the applicator at an angle between 30° and 60°, preferably 45°, with respect to a horizontal plane, preferably a guide protrusion (7) protruding from the oval rim which serves as a guide for holding open the lower eyelid of the eye; and,
an attachment portion (8) located on the structure provided with grips, for receiving and holding in a fixed position a single-dose container. The applicator device keeps the single-dose container isolated from any physical contact with flat external surfaces. In another preferred embodiment, the attachment portion (8) comprises a stop protrusion that functions as a stop mechanism for inserting the single-dose container up to a certain point and locking its displacement.

The oval rim, which ergonomically conforms to the curvature of the eye, firmly holds the lower and upper eyelid and prevents blinking during application of the eye drop, allowing the drop to be applied to the eye with complete safety and confidence, eliminating out-of-eye applications caused by patient trembling or inexperience.

The features of the ophthalmic solution applicator described above also make it possible to use the single-dose container for applications after the first use.

The present invention also relates to a kit for ophthalmic solutions comprising a bottle (10) with an airtight cap which in turn contains the applicator for ophthalmic solutions described above. The capped bottle allows isolating from the environment the applicator with the single-dose container inside it, enabling the safe use of the single-dose container in applications after the first use, eliminating the risk of contamination by contact with the dropper spout of the single-dose vial during handling and installation of the entire contents of the single-dose vial.

DETAILED DESCRIPTION OF THE INVENTION

Some preferred embodiments of the present invention are described below, which are not intended to limit the scope of protection of the claims in any way.

Figure 1:
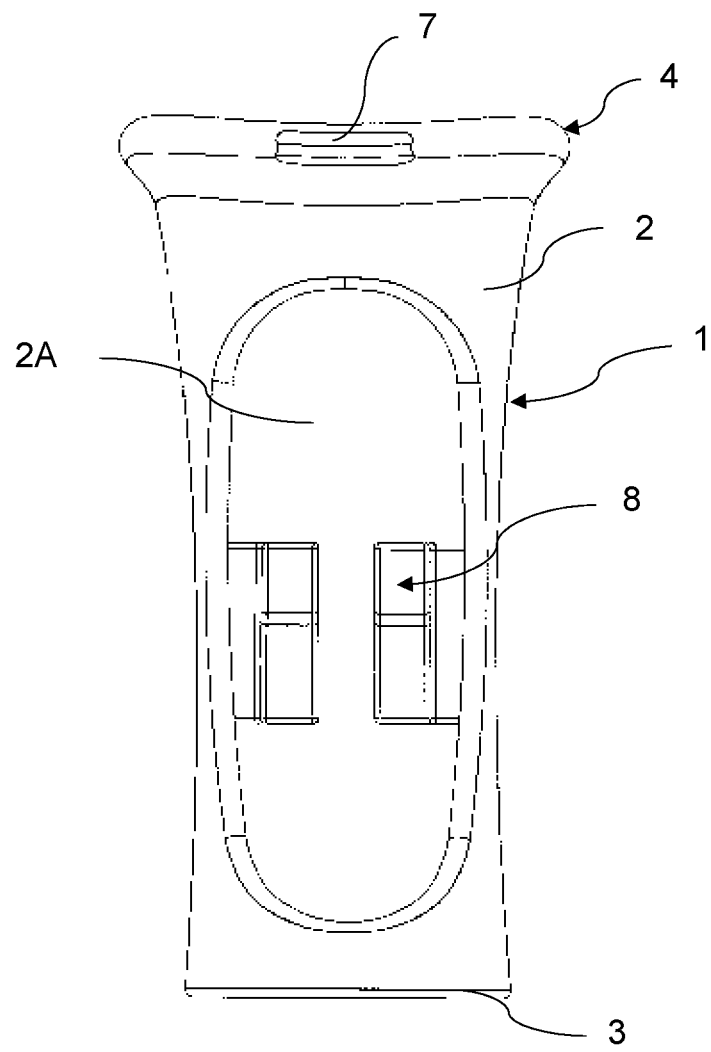
FIG. 1: Shows a front view of the applicator.

In a preferred embodiment, the structure (1) comprises two side walls, as shown in FIG. 1, which leave a substantially open space (2A) at the front and rear of the applicator.

Figure 2:
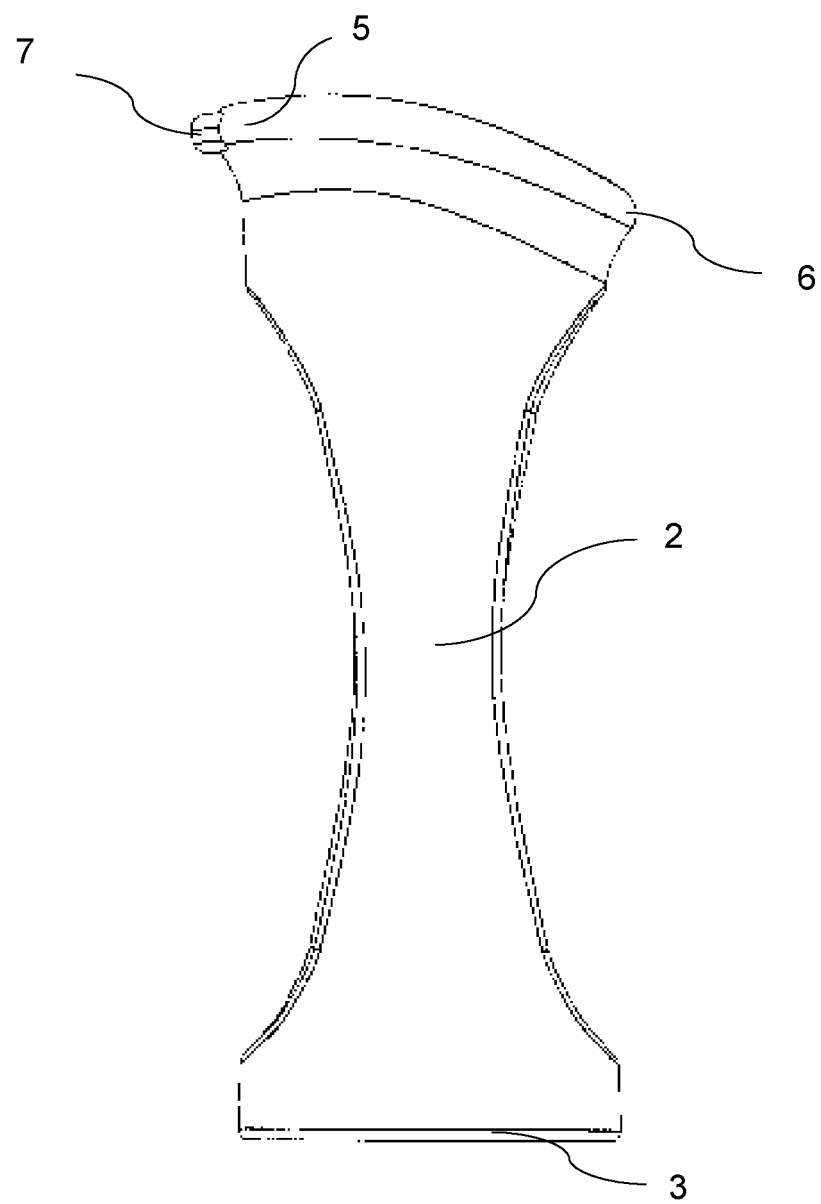
FIG. 2: Shows a side view of the applicator.

FIG. 2 shows how the attachment portion (8) is kept within the side walls of the structure (1), in such a way that it cannot be seen from the side, so as not to cause discomfort when handling the container. In this configuration the walls have a concave curvature so that the fingers can be inserted through it without difficulty.

Figure 3:
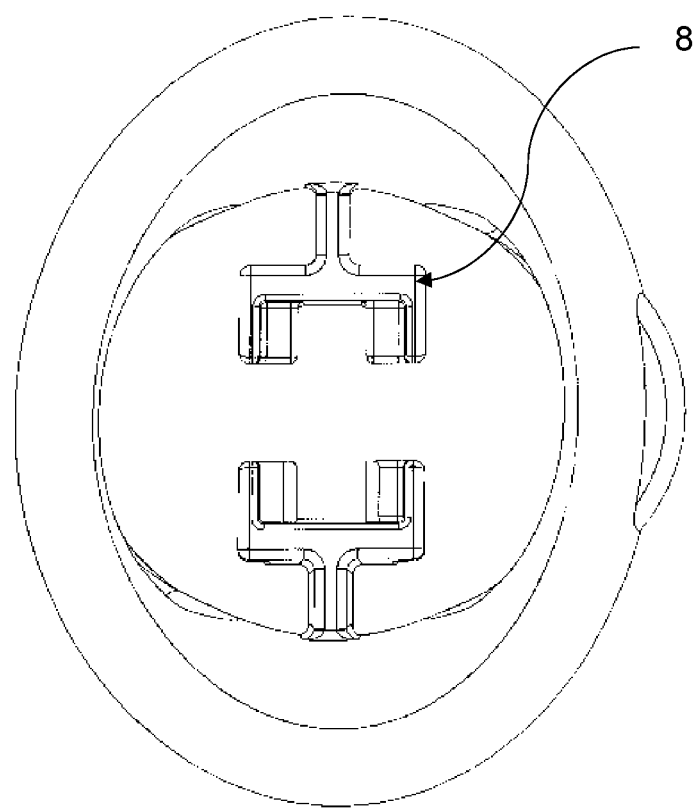
FIG. 3: Shows a plan view of the applicator.
Figure 4:
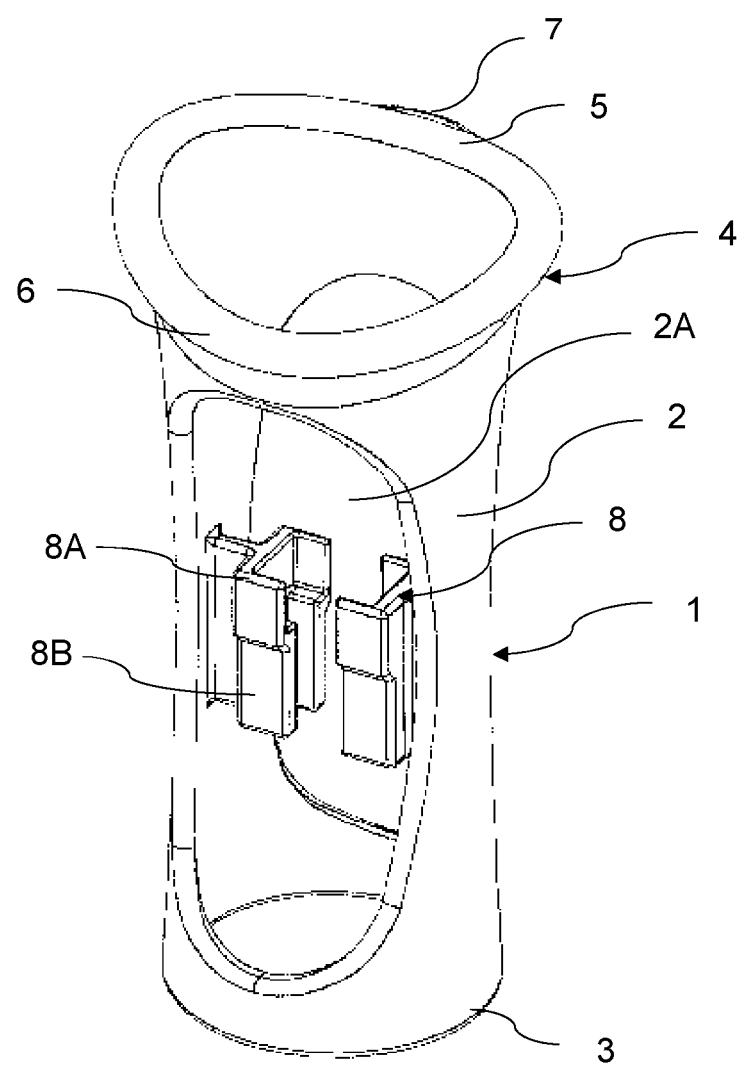
FIG. 4: Shows a perspective view of the applicator.
Figure 5:
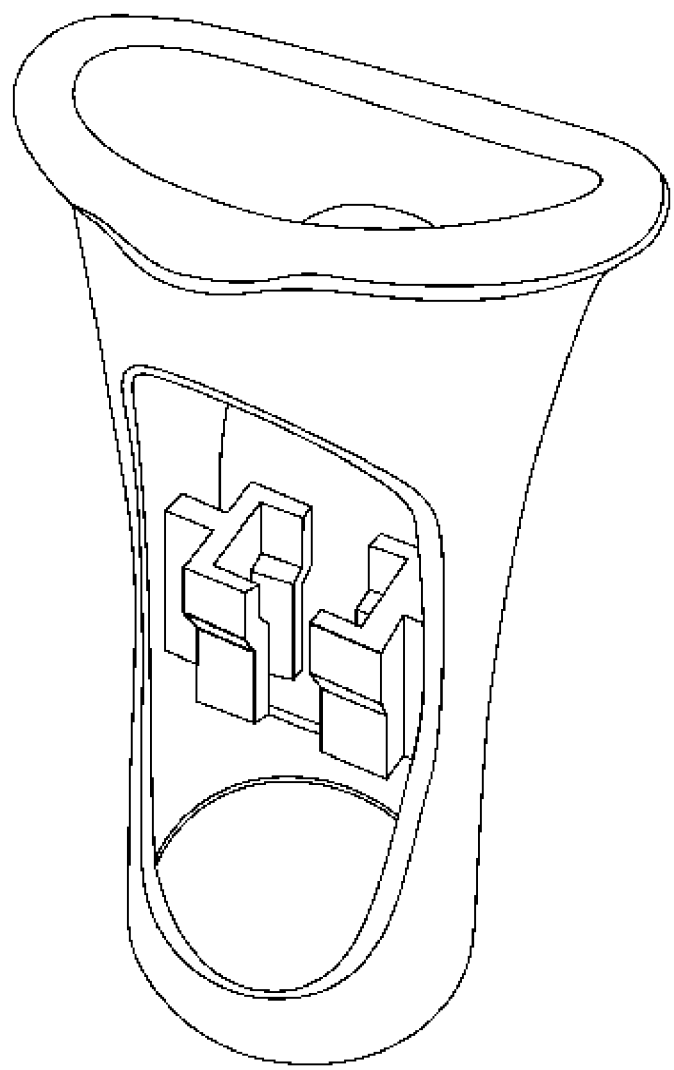
FIG. 5: Shows a perspective view of the back side of that shown in FIG. 4.
Figure 6:
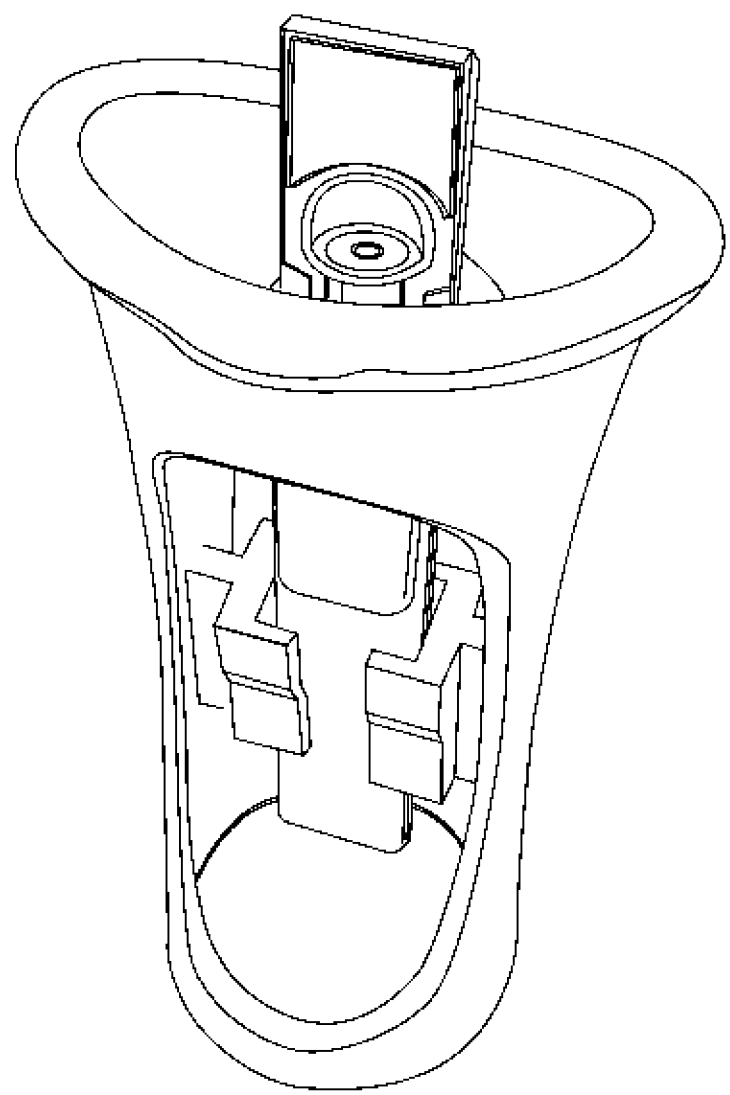
FIG. 6: Shows a perspective view of the applicator with the single-dose container in place.
Figure 7:
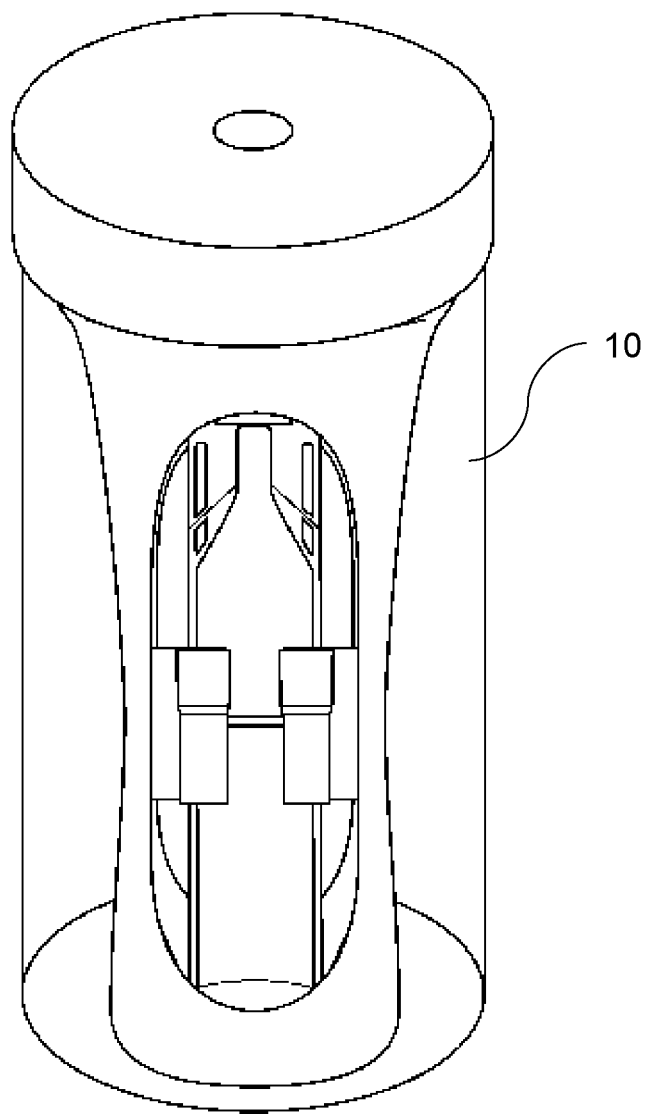
FIG. 7: Shows the capped bottle of the kit with the applicator and container inside.
Figure 8:
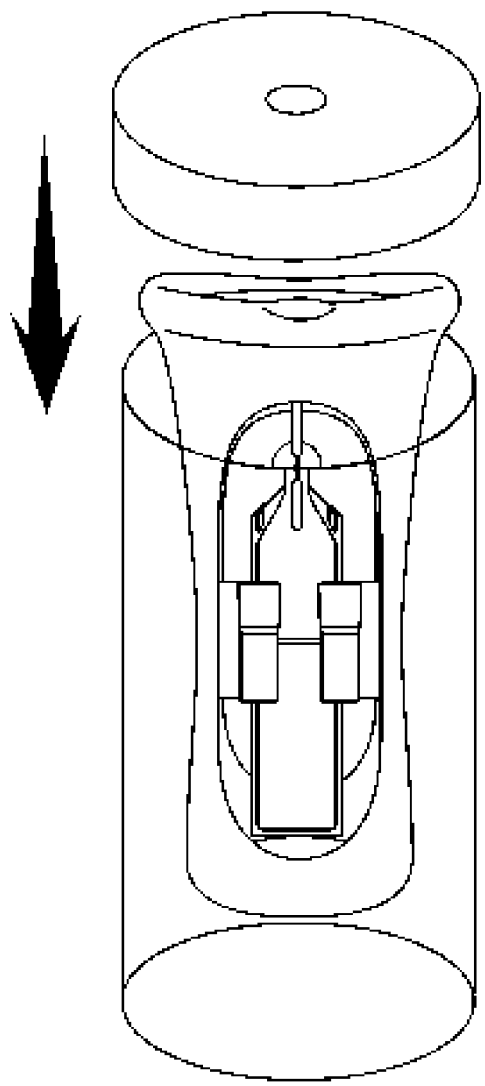
FIG. 8: Shows the action of inserting the applicator with single-dose container into the capped bottle.
Figure 9:
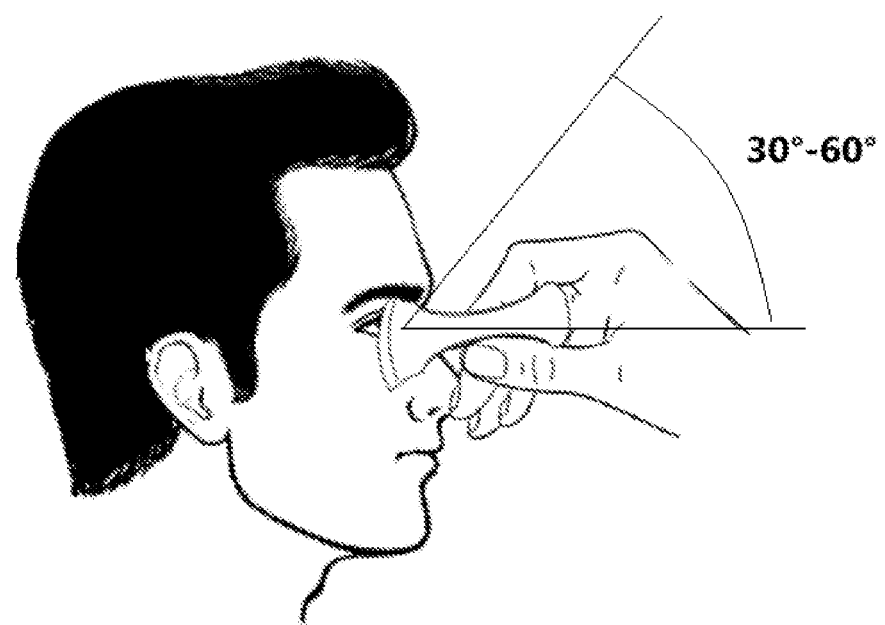
FIG. 9: Shows the preferred angle of 45° for placement of the device on the eye.

FIGS. 3 and 4 show in greater detail a preferred embodiment of the attachment portion (8) wherein a handle is arranged on each side wall, each handle having a flat profile coupled to a first C-shaped profile (8A), wherein the single-dose container can be coupled between the first C-shaped profiles. In greater detail, each first C-shaped profile comprises a second C-shaped profile (8B) arranged adjacent and continuous to the first C-shaped profile (8A), wherein said second C-shaped profile (8B) is of a smaller size than the first C-shaped profile (8A) and its function is to serve as a stop mechanism to engage the container in the center at a certain fixed position and prevent it from moving further. The advantage of making the attachment portion with a C-shaped profile is that the entire applicator can be made from a single material as a single piece, preferably from plastic. The C-shape of the attachment portion keeps the tip of the dropper in a centered and secure position, which allows the drop to be applied to the eye with complete safety and confidence, eliminating out-of-eye applications caused by patient trembling or inexperience (which is quite common during the application of eye drops using single-dose applicators and ophthalmic application bottles). In another preferred embodiment, the inner space of each second C-shaped profile is gradually tapered, the inner space being inclined as a wedge to lock the container as it advances into the applicator.

Also, in another preferred embodiment, the grip is an opening with a plurality of flexible fins around it that converge at a central point. Likewise, the figures show the hollow, flat part of the support base for the insertion of a finger allowing the single-dose container to be removed.

In another preferred embodiment, the applicator device is made of a bacteriostatic or bactericidal material such as, for example, plastic material containing silver ions.

In another preferred embodiment, a ring of a flexible material such as rubber, silicone, soft plastic or the like is attached to the oval rim to soften the positioning of the device upon contact with the periphery of the eye.

In another preferred embodiment, the airtight bottle of the kit for ophthalmic solutions is cylindrical and made of a transparent material to allow the label and the contents inside to be seen, and the cap is round. Likewise, the capped bottle can be made of a bacteriostatic or bactericidal material such as, for example, plastic material containing silver ions.

The invention claimed is:

1. An applicator for ophthalmic solutions in single-dose containers, comprising:
   a structure (1) with one or more walls (2) covering a length, a width and a height of a single-dose container, wherein the one or more walls (2) leave at least one open space for inserting, removing, pressing the single-dose container, and allowing a label and contents of the container to be viewed;
   a flat hollow support base (3) attached to or forming part of one end of the one or more walls of the structure;
   an oval rim (4) located at the other end of the one or more walls of the structure, the oval rim having an upper lip (5) and a lower lip (6) that are concave, where the upper lip (5) is placed at a different level from the lower lip (6), to facilitate positioning of the applicator at an angle between 30° and 60° to a horizontal plane; and
   an attachment portion (8) located in the structure having two handles for receiving and holding in a fixed position the single-dose container; and, where each handle comprises a first C-shaped profile (8A) and each handle comprises a second C-shaped profile (8B) arranged adjacent and continuous to the first C-shaped profile (8A), wherein said second C-shaped profile (8B) is of a smaller size than the first C-shaped profile (8A) and its function is to serve as a stop mechanism to engage a center of the single-dose container at a certain fixed position and prevent the single-dose container from moving further.

2. The ophthalmic solution applicator according to claim 1, wherein on the upper lip of the oval rim there is a protruding guide (7) which serves as a guide to keep a lower eyelid of an eye open.

3. The ophthalmic solution applicator according to claim 1, wherein the attachment portion is an opening with a plurality of surrounding fins converging at a central point.

4. The ophthalmic solution applicator according to claim 1, wherein the attachment portion comprises a stop for inserting the single-dose container up to a certain point.

5. The ophthalmic solution applicator according to claim 1, wherein the applicator is made of a bacteriostatic or bactericidal material.

6. The ophthalmic solution applicator according to claim 5, wherein the bacteriostatic material comprises silver ions.

7. The ophthalmic solution applicator according to claim 1, wherein the oval rim (4) includes a ring of a flexible material to soften the positioning of the device.

8. A kit for ophthalmic solutions characterized by comprising a bottle (10) with an airtight cap which contains a solution applicator device, and the solution applicator device comprises:

a structure (1) with one or more walls (2) covering a length, a width and a height of a single-dose container, wherein the one or more walls (2) leave an open space for inserting, removing, pressing the single-dose container and allowing the label and the contents of the container to be viewed;

a flat hollow support base (3) attached to or forming part of one end of the one or more walls of the structure;

an oval rim (4) located at the other end of the one or more walls of the solid structure, the oval rim having an upper lip (5) and a lower lip (6) that are concave, where the upper lip (5) is placed at a different level from the lower lip (6) to facilitate positioning the applicator at an angle between 30 and 60° to a horizontal plane; and an attachment portion (8) located in the structure having two handles for receiving and holding in a fixed position the single-dose container; where each handle comprises a first C-shaped profile (8A) and each handle comprises a second C-shaped profile (8B) arranged adjacent and continuous to the first C-shaped profile (8A), wherein said second C-shaped profile (8B) is of a smaller size than the first C-shaped profile (8A) and its function is to serve as a stop mechanism to engage the single-dose container in the center at a certain fixed position and prevent the single dose container from moving further.

9. The kit for ophthalmic solutions according to claim 8, wherein the bottle is cylindrical, made of a transparent material and the airtight cap is round.

10. The kit for ophthalmic solutions according to claim 9, wherein the bottle and the airtight cap are made of a bacteriostatic material containing silver ions.

11. The ophthalmic solution applicator according to claim 1, wherein the oval rim (4) includes a ring of a flexible material to soften the positioning of the single-dose container.

* * * * *